United States Patent [19]

Puschmann

[11] Patent Number: 4,547,154
[45] Date of Patent: Oct. 15, 1985

[54] DEVICE FOR THE ENCAPSULATION IN PLASTER OF MODELS OF THE JAW FOR THE MANUFACTURE OF DENTAL PROSTHESES

[76] Inventor: Johannes Puschmann, Landshuter Strasse 4, 8252 Taufkirchen, Fed. Rep. of Germany

[21] Appl. No.: 674,699
[22] PCT Filed: Apr. 11, 1984
[86] PCT No.: PCT/EP84/00111
   § 371 Date: Nov. 26, 1984
   § 102(e) Date: Nov. 26, 1984
[87] PCT Pub. No.: WO84/04034
   PCT Pub. Date: Oct. 25, 1984

[30] Foreign Application Priority Data
Apr. 12, 1983 [DE] Fed. Rep. of Germany ....... 3313198

[51] Int. Cl.[4] ............................................. A61C 19/00
[52] U.S. Cl. ........................................ 433/49; 433/56; 433/65
[58] Field of Search ...................... 433/49, 50, 54, 55, 433/56, 57, 58, 59, 63, 65, 69

[56] References Cited

U.S. PATENT DOCUMENTS

| | | | |
|---|---|---|---|
| 2,270,561 | 1/1942 | Sanborn | 433/63 |
| 3,130,494 | 4/1964 | MacKay | 439/69 |
| 3,439,421 | 4/1969 | Perkowski | 433/56 |
| 3,693,260 | 9/1972 | Hernandez | 433/56 |
| 3,808,688 | 5/1974 | Guichet | 433/55 |
| 4,155,163 | 5/1979 | Schwartz | 433/56 |
| 4,189,835 | 2/1980 | Seldin | 433/55 |

FOREIGN PATENT DOCUMENTS 2066667 1/1981 United Kingdom ................. 433/56

Primary Examiner—John J. Wilson
Attorney, Agent, or Firm—Stiefel, Gross, Kurland & Pavane

[57] ABSTRACT

A device for the encapsulation in plaster of jaw models for the manufacture of dental prostheses, including an articulator having a lower model support for a lower-jaw template and an upper model support for an upper-jaw template, the upper model support being pivotal relative to the lower model support around the condylar axis; and for the patient-specific adjustment of the bite plane, a frame having a bottom plate for setting up the articulator. The frame has a fastening device for fixing the condylar axis relative to the bottom plate, and a table which is parallel to the bottom plate and whose surface determines the bite plane and is displaceable vertically and sagitally with respect to the condylar axis.

9 Claims, 8 Drawing Figures

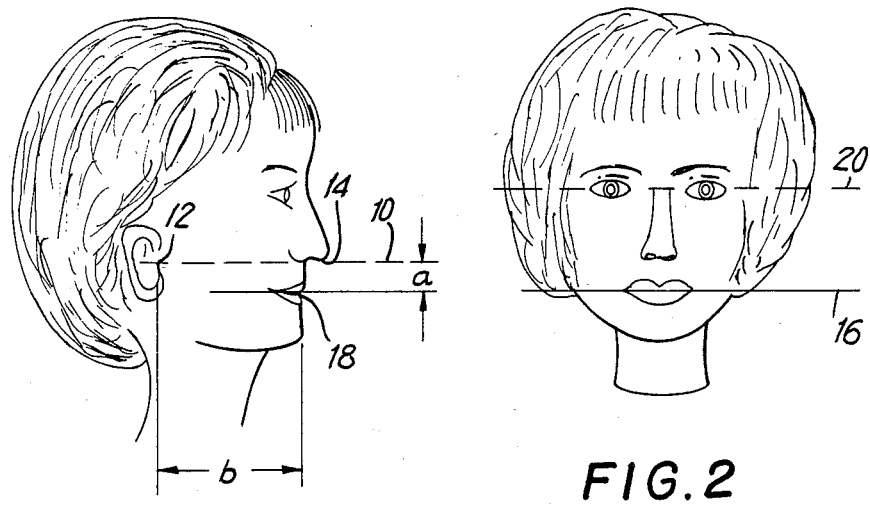
FIG.1
FIG.2
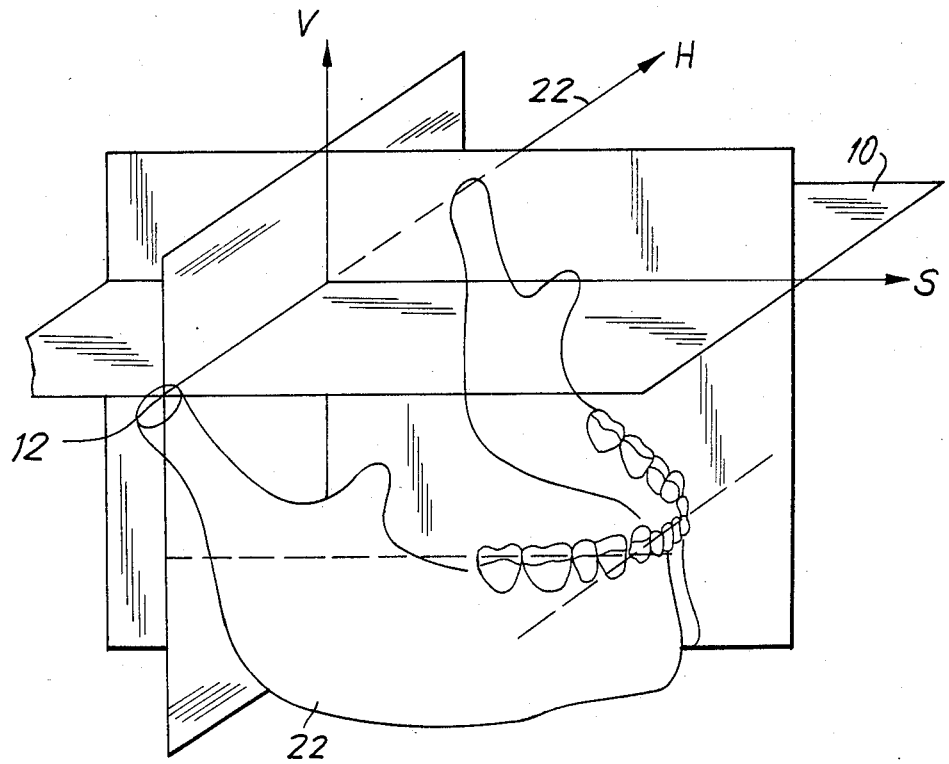
FIG.3

DEVICE FOR THE ENCAPSULATION IN PLASTER OF MODELS OF THE JAW FOR THE MANUFACTURE OF DENTAL PROSTHESES

TECHNICAL FIELD

The present invention relates to a device for the encapsulation in plaster of models of the jaw for the manufacture of dental prostheses. More particularly, it relates to such a device useful in producing a prosthesis of the type having an articulator which has a lower model support for a lower-jaw template and an upper model support for an upper jaw template, the upper model support being swingable relative to the lower model support around a horizontal axis, the condylar axis.

BACKGROUND ART

For the production of a prosthesis it has heretofore been generally customary for a dentist to take a manual impression of the bite, by which he determines, without the aid of instruments, the association between the lower jaw and the upper jaw. A template with wax occlusal guides is made in the toothless mouth of the patient, the guides representing the two rows of teeth. For the manufacture of the prosthesis, the two templates are fastened to the upper and lower model supports, respectively, of an articulator in a dental laboratory. In most cases these articulators are so-called average value articulators with which the plane of the bite is determined.

The object of the present invention is to so improve a device of the aforementioned type that a prosthesis which is adapted to the individual patient and is designed to conform to his particular bite plane, can be produced by means which are relatively simple and easy to handle.

Other objects and advantages of the invention will be apparent from the following detailed description of a preferred embodiment thereof.

DISCLOSURE OF THE INVENTION

In accordance with the present invention, the preceding objects are achieved employing a frame having a bottom plate for setting up the articulator, a fastening device for fixing the condylar axis relative to the bottom plate, and a table which is parallel to the bottom plate and whose upper surface determines the bite plane and is adjustable vertically and sagitally with respect to the condylar axis.

The invention provides the dental technician with an apparatus which may be employed with conventional commercial articulators, and be utilized to adjust the condylar axis. By displacement of the table in vertical and sagittal directions corresponding to the data measured on the individual patient, the bite plane can be determined individually.

For the determination on the patient of the data necessary for the adjustment of the table there is used a U-shaped bite fork, the arcuate vertex of which is connected to a front strip which can be aligned parallel to the bipupillary line and which passes on both sides into respective arms, which arms can be aligned parallel to Camper's line. In accordance with preferred forms of the invention, one arm bears a measurement scale whose zero point is on the top side of the arm and corresponds to the arcuate vertex of the bite fork; and a slide, which bears a vertically extending measurement scale, is displaceable on one arm.

BRIEF DESCRIPTION OF DRAWINGS

Further features and advantages of the invention will become evident from the following description of the preferred embodiment illustrated in the drawings, in which:

FIG. 1 is a side elevation of a human head, serving to show the bite plane and Camper's plane;

FIG. 2 is a front elevation of the head, showing the bipupillary line;

FIG. 3 is a perspective of the lower jaw of a human with the corresponding coordinate system;

FIG. 1 shows, in side elevation, a human head with the so-called Camper's plane 10 illustrated. The Camper's plane 10 is an imaginary plane which extends through the two condyle points 12 and the subnasal point 14. It is approximately parallel to the bite plane 16 of the patient and at a distance a from it.

FIG. 1 also illustrates the distance b between the condyle point 12 and the front edge 18 of the upper row of teeth or of an upper-jaw bite template.

Figure 4:
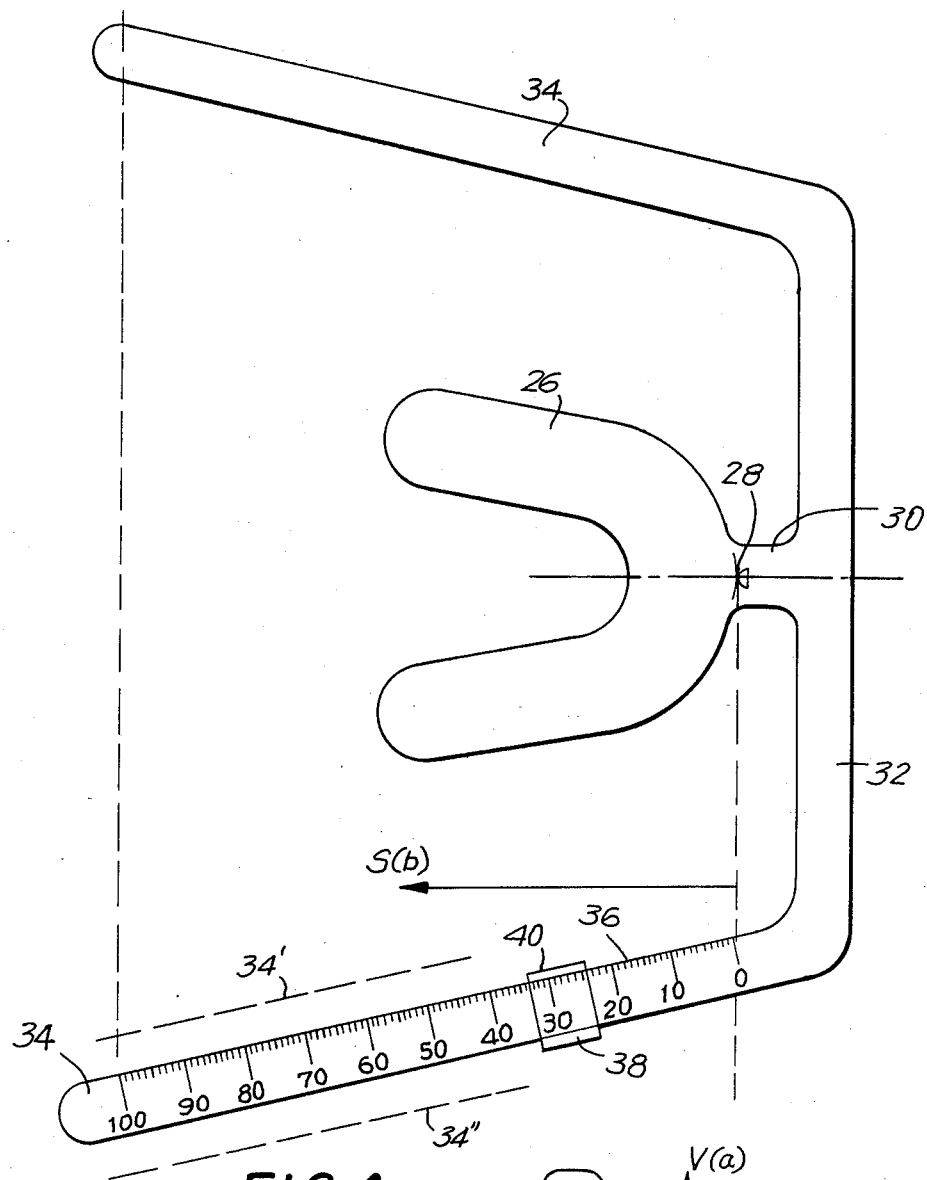
FIG. 4 is a top view of a bite fork according to the invention.

From FIG. 2 it may be seen that the bite plane 16 extends parallel to the bipupillary line 20.

FIG. 3 shows, in perspective, a lower jaw 22 and a three-dimensional coordinate system having a vertical axis V, a horizontal axis H and the sagittal axis S. The horizontal axis H connects the two condyle points 12 and is thus identical to the condylar axis 22. The latter lies in Camper's plane 10 which, as previously mentioned, is parallel to and at a distance a above the bite plane.

Figure 6:
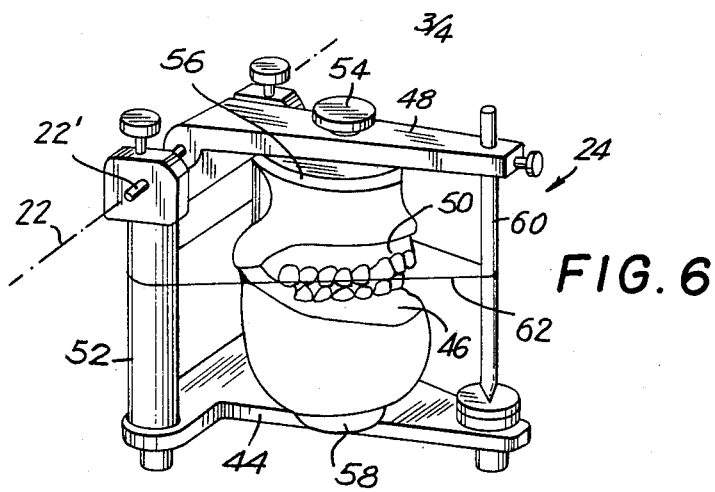
FIG. 6 is a perspective of a conventional, commercial average-value articulator.

In practice, prostheses are produced by means of a manual bite impression. A conventional commercial, average-value articulator 24 (FIG. 6) used in the production of such prostheses is designed without regard to the distances a and b, shown in FIGS. 1 and 2, which differ for each patient.

Figure 5:
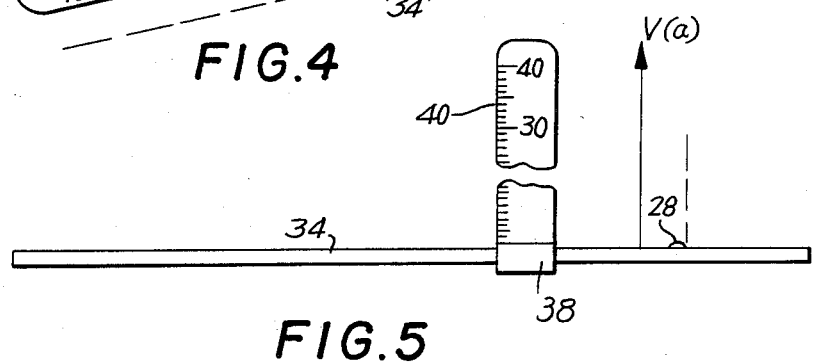
FIG. 5 is a side view of the bite fork.

FIGS. 4 and 5 show a bite fork 26 in accordance with the invention. The bite fork is bent into a U-shape, has a small protuberance or elevation 28 at the vertex of the arch, and is connected via a web 30 to a front strip 32. The front strip 32 passes on each of its sides into a respective arm 34. The two arms 34, the front strip 32 and the bite fork 26 lie in the same plane. Corresponding to the different shapes of patients' heads, different size bite forks can be used, the two arms lying closer together (dashed line 34') for use with a patient having a narrow head than for use with a patient having a broad head (dashed line 34").

As shown in FIG. 4, one arm 34 is provided, according to the invention, with a measurement scale 36 whose zero point corresponds to the vertex of the arch (at elevation 28) of the bite fork 26. As may be seen in the drawing, the zero point of the measurement scale 36 is not precisely perpendicularly below the vertex of the arch but is displaced by an amount which takes into account the angle between the arm 34 and the front strip 32.

On the arm 34 a slide 38 bearing a vertically extending measurement scale 40 is displaceably mounted. The zero point of this measurement scale 40 lies on the top side of the arm 34.

In order to determine the distances a and b shown in FIG. 1 on an individual patient, the bite fork is placed in the mouth in such a manner that the elevation 28 rests against the front edge of the upper-jaw bite template at its center. The upper jaw bite template is placed on the patient parallel to the Camper's plane 10, the front strip 32 of the bite fork 26 being aligned parallel to the bipupillary line 20. By means of the slide 38 and the measurement scale 40 fastened to it, the distance a to Camper's plane 10 can be read; for this purpose the condyle point 12 is initially determined on the patient. Simultaneously with this measurement, the distance b is read off the measurement scale 36 by means of the slide 38, which is moved to the condyle point 12.

Figure 7:
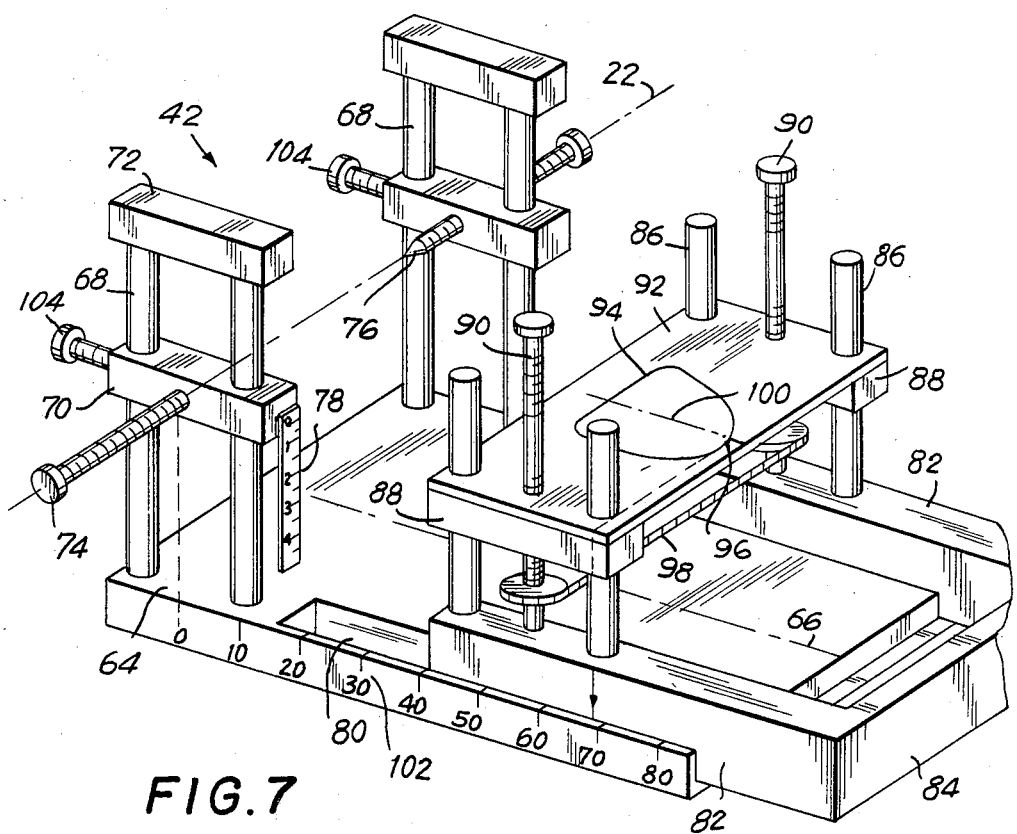
FIG. 7 is a perspective of a frame according to the invention, adapted to receive an articulator.
Figure 8:
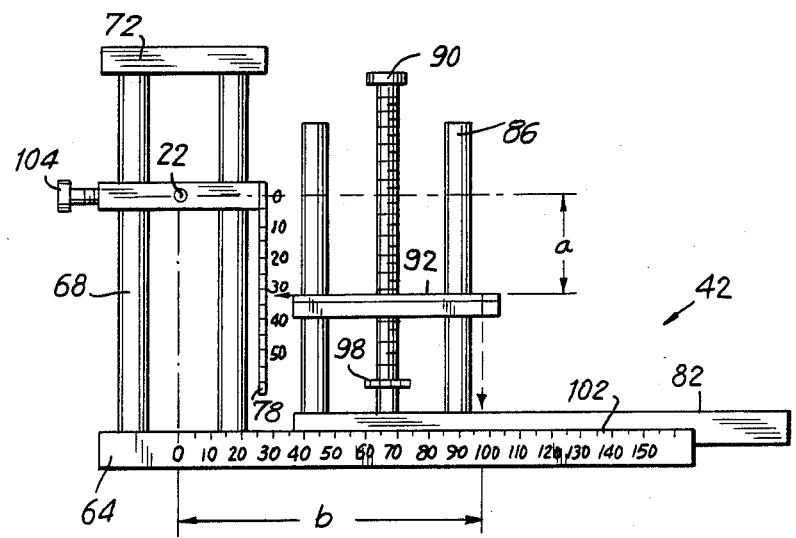
FIG. 8 is a side elevation, on a reduced scale, of the frame of FIG. 7.

The transfer of these values a and b, measured in millimeters, to the articulator 24 is effected by means of the frame 42 illustrated in FIGS. 7 and 8. Before the latter is explained in further detail, the main components of the known articulator 24, shown in FIG. 6, may be briefly indicated. The articulator 24 has a lower model support 44 for a lower-jaw model 46 as well as an upper model support 48 for an upper jaw model 50. On the lower model support 44 there are fastened two condylar columns 52 between which the upper model support 48 is mounted to pivot about the condylar axis 22. From this condylar axis 22, two stub shafts 22' extend laterally outwardly from the condylar columns 52.

A mounting plate 56 is fastened on the upper model support 48 by means of a mounting screw 54, the model of the upper jaw 50 being fastened on it. The lower model support 44 also has, in corresponding manner, a mounting plate 58 for the lower-jaw model 46. By means of a vertical incisal pin 60 the two model supports 44 and 48 may be adjusted parallel to each other. Corresponding to the average values present in practice, circumferential notches are made both in the incisal pin 60 and in the two condylar columns 52, within which notches a rubber band 62 is fixed, the position of the bite plane based on the average values being thereby determined.

In order to adjust the bite plane independently of these average values and as a function of the patient-specific distances a and b, the articulator 24 is placed within frame 42 illustrated in FIGS. 7 and 8. This frame has a bottom plate 64 with a flat surface on which the sagittally extending longitudinal central axis 66 is indicated. The bottom plate 64 bears two vertical columns 68 at one end of each of its longitudinal sides. On each pair of these columns a slide 70 is guided in vertically displaceable manner. At their upper ends the two columns 68 of each pair are connected to each other by a cross member 72.

A horizontally extending fastening screw 74 is screwed into each slide 70 in such a manner that its point 76 faces the opposite fastening screw 74 and is coaxial with it. The condylar axis 22 is determined by the two fastening screws 74.

One of the two slides 70 bears a vertically extending scale 78 whose zero point lies at the height of the condylar axis 22.

As further illustrated in FIG. 7, the bottom plate 64 is provided on its two longitudinal sides with guides 80 which extend in sagittal direction, each of which receives a carriage 82. The two carriages 82 are firmly connected to one another by a grip strip 84.

On each carriage 82 there is fastened two vertical columns 86 on which a slide 88 is vertically displaceable by means of an adjustment spindle 90. The adjustment spindles 90 are connected to one another by a chain drive 98 or the like, in order that a table 92 which is supported by the slides 88 and extends parallel to the bottom plate 64 is displaced in parallel relation to the bottom plate. The top surface of the table 92 has an arcuate reference line 94 for the upper-jaw model 50, whose front arcuate vertex 96 lies in the center of the table (sagittal center line 100) and is projected parallel to the condylar axis 22 onto a reading mark (arrow) on a carriage 82.

On the longitudinal side of one guide 80 there is a scale 102 whose zero point lies vertically below the condylar axis 22.

For the adjustment of the patient-specific bite plane 16, the conventional commercial articulator 24 is so positioned on the bottom plate 64 of frame 42 that the condylar axis 22 (stub shaft 22') lies in the same vertical plane as the longitudinal central axis of the two fastening screws 74. The two slides 70 are then displaced on the columns 68 until the condylar axis 22 of the articulator 24 coincides with the longitudinal central axis of the two fastening screws 74. The two slides are fixed in this position by the fastening screws 104. The two fastening screws 74 are then screwed in until their tips 76 grasp the stub shafts 22' of the articulator 24 and thus fix the condylar axis 22. In this connection the articulator 24 should be aligned centrally with respect to the longitudinal central axis 66 of the bottom plate 64.

The table 92 is then moved by the carriage 82, which is displaceable in the two guides 80, proximate to the scale 78 such that the distance a from the surface of the table 92 can be set on scale 78. The two adjustment spindles 90, which are coupled to each other by the chain drive 98, are used for adjusting the height of the table.

After the vertical distance a of the bite plane 16 from Camper's plane 10 has been thus established, the table 92 is further displaced, as also shown in FIG. 8, until the vertex 96 of the arch of the reference line 94 is at the previously determined distance b from the condylar axis 22. This distance b can be set on the scale 102 by the arrow on the one carriage 82.

The two individual values a and b are thus established. Thereupon the upper-jaw template of the patient can be centered, corresponding to the reference line 94, on the surface of the table 92. The function impression is then fastened on the upper-jaw template by plaster in known manner on the upper model support 48 of the articulator 24.

In this manner a very accurate, patient-specific positioning of the upper-jaw template is established. On the basis of this position, a partial or full prosthesis can be made. The parallel position of table 92 and bottom plate 94 assures a parallel encapsulation with plaster in the articulator 24.

The articulation of the lower jaw to the upper jaw can then be effected in known manner, and need not be further described.

In accordance with the present invention, the application of the frame 42 is not limited to a total prosthesis; full-teeth and partial-teeth jaw models can also be precisely encapsulated in plaster for all average-value articulators in the Bonwill triangle or, after determination of the two distances a and b, can be articulated-in, in a manner specific to the individual patient, by means of the bite fork 96 shown in FIGS. 4 and 5.

When the table 92 with the carriage 82 is removed from the frame 42, the frame can also be used as a mounting aid for facial arches and the corresponding articulators; for this purpose the facial arches are clamped fast on the two cross members 72.

While there has been described and illustrated a preferred embodiment of the present invention, it will be understood that various changes may be made in the preceding description without departing from the scope of this invention.

I claim:

1. In a device for the encapsulation in plaster of jaw models for the manufacture of dental prostheses, having an articulator which has a lower model support for a lower-jaw template and an upper model support for an upper-jaw template, the upper model support being swingable relative to the lower model support around the horizontal condylar axis, the improvement comprising:
    a frame having a bottom plate for supporting the articulator,
    means for fixing the condylar axis relative to the bottom plate, and
    a table parallel to the bottom plate and having a top surface which determines the bite plane and is adjustable vertically and sagitally with respect to the condylar axis.

2. The device according to claim 1, wherein the means for fixing the condylar axis comprises guide means secured to the bottom plate of said frame, vertically displaceable slide means mounted on said guide means, and a pair of spaced apart, coaxial fastening means engaged in and supported by said slide means.

3. The device according to claim 2, wherein the slide means includes a vertically extending scale with zero point at the height of the condylar axis for adjustment of the height of said table.

4. The device according to claim 1, wherein said bottom plate has, on its two longitudinal sides, guide means extending in the sagittal direction, said guide means receiving displaceable carriage means, and vertical displacement means mounted on said carriage means for vertically displacing said table.

5. The device according to claim 4, wherein said vertical displacement means comprises slide means supporting said table and adapted to be vertically displaceable and lockable.

6. The device according to claim 4, further comprising a scale having a zero point vertically below the condylar axis adjacent said guide means for adjustment of said table in the sagittal direction.

7. The device according to claim 6, wherein the top surface of said table is provided with an arcuate reference line for the upper-jaw template, the front arcuate vertex of which lies in the center of the table.

8. A device for the manufacture of a bite prosthesis, according to claim 1, comprising a U-shaped bite fork whose arcuate vertex is connected to a front strip adapted to be aligned perpendicular to the bipupillary line and which is integral with a pair of side arms, which are adapted to be aligned parallel to the Camper's line, and further comprising a measurement scale on one of said arms, whose zero point corresponds to the arcuate vertex of said bite fork.

9. The device according to claim 8, further comprising slide means displaceably mounted on one of said side arms and bearing a vertically extending measurement scale, the zero point of the scale lying on the top side of said side arm.

* * * * *